United States Patent [19]

Fong

[11] Patent Number: 5,524,038
[45] Date of Patent: Jun. 4, 1996

[54] METHOD OF NON-DESTRUCTIVELY INSPECTING A CURVED WALL PORTION

[75] Inventor: James T. Fong, Bethel Park, Pa.

[73] Assignee: The United States of America as represented by the United States Department of Energy, Washington, D.C.

[21] Appl. No.: 367,604

[22] Filed: Jan. 3, 1995

[51] Int. Cl.$^6$ .................................................. G01N 23/04
[52] U.S. Cl. ................................................ 378/4; 378/58
[58] Field of Search .............................. 378/4, 8, 9, 11, 378/14, 17, 19, 20, 51, 57, 58, 59

[56] References Cited

U.S. PATENT DOCUMENTS

| | | | |
|---|---|---|---|
| 4,785,354 | 11/1988 | Nakamura et al. | 378/4 |
| 4,845,769 | 7/1989 | Burstein et al. | 378/58 |
| 4,907,157 | 3/1990 | Uyama et al. | 378/11 X |

*Primary Examiner*—David P. Porta
*Attorney, Agent, or Firm*—Virginia B. Caress; William B. Moser; Paul A. Gottlieb

[57] ABSTRACT

A method of non-destructively inspecting a curved wall portion of a large and thick walled vessel for a defect by computed tomography is provided. A collimated source of radiation is placed adjacent one side of the wall portion and an array of detectors for the radiation is placed on the other side adjacent the source. The radiation from the source passing through the wall portion is then detected with the detectors over a limited angle, dependent upon the curvature of the wall of the vessel, to obtain a dataset. The source and array are then coordinately moved relative to the wall portion in steps and a further dataset is obtained at each step. The plurality of datasets obtained over the limited angle is then processed to produce a tomogram of the wall portion to determine the presence of a defect therein. In a preferred embodiment, the curved wall portion has a center of curvature so that the source and the array are positioned at each step along a respective arc curved about the center. If desired, the detector array and source can be reoriented relative to a new wall portion and an inspection of the new wall portion can be easily obtained. Further, the source and detector array can be indexed in a direction perpendicular to a plane including the limited angle in a plurality of steps so that by repeating the detecting and moving steps at each index step, a three dimensional image can be created of the wall portion.

8 Claims, 2 Drawing Sheets

METHOD OF NON-DESTRUCTIVELY INSPECTING A CURVED WALL PORTION

FIELD OF THE INVENTION

The present invention relates generally to a method for non-destructively inspecting a curved wall portion of a vessel, and more particularly to a method which can be used to identify a defect(s) by producing a computed tomogram of the wall portion using a limited viewing angle.

BACKGROUND OF THE INVENTION

A conventional computed tomography (CT) system includes a radiation source, a detector array, an object positioning unit between the source and the detector, a computer unit with image processing subsystems, and a color graphic image display subsystem. The radiation source is either an x-ray tube, an x-ray linear accelerator, or a gamma-ray emitting radioisotope which emits a flux of photons. The photons from the radiation source are highly collimated (focused) to form a thin fan-shaped beam which is directed at the object of interest (to be examined). The fan beam is typically adjustable, for example from 10 to 35 degrees wide and from 1 to 5 mm thick.

During a scan of the object, high energy photons from the radiation source passing through the object are highly collimated upon entering the detector array. The detectors convert the photons into visible analog light events, and these are then digitized by proprietary current-integration electronics into datasets. The scanned datasets are computer processed to calculate density matrices, in order to electronically reconstruct the object's image in the plane of the beam. The reconstructed image is passed onward to graphics display routines for analysis and video display. The image information is typically analyzed with proprietary software programs to extract precise density and dimensional information.

Tomograms of defects are developed by rotating the object in the radiation beam, or the source-detector arrangement, to provide opacity measurements along many interior axes. A typical scan includes thousands of measurements. Projection data computed over 180° (a series of scans along a plane starting at one side and continuing to the other—i.e. ±90° from a middle) produce an image which is a two-dimensional cross section. Three-dimensional images are then generated by making successive scans along the height of the object.

Nuclear reactor vessels and the like have circular walls with relatively large thicknesses of steel. Due to this thickness, a typical long metal chord length of 48"–63" is encountered through which the photons of any practical source cannot pass to complete the desired scans. Thus, a conventional computed tomogram is not practical for such large and thick walled vessels. Obviously, the extreme size and weight of the vessel also makes it difficult to perform the necessary 180° scans.

It will also be appreciated that conventional radiographs of such vessels currently used have problems with detecting of cracks of negligible width perpendicular to the beam direction. This is due to negligible density changes in the vessel wall under inspection.

SUMMARY OF THE INVENTION

In accordance with the present invention, a method of non-destructively inspecting a curved wall portion of a large and thick walled vessel for a defect by producing a tomogram of the wall portion is provided. The method includes the initial steps of placing a collimated source of radiation adjacent one side of the wall portion and of placing an array of detectors for the radiation on the other side of the wall portion adjacent the source. The radiation from the collimated source passing through the wall portion is then detected with the detectors over a limited angle, dependent upon the size of the vessel and wall curvature, from a normal to the wall portion from the source to obtain a dataset. The source and detector array are then coordinately moved typically by a common fixture relative to the wall portion in steps between projected vertices of the limited angle and a further dataset is obtained at each step. The plurality of datasets obtained over the limited angle is then processed to produce a tomogram of the wall portion and hence to determine the presence of a defect in the wall portion.

In a preferred embodiment, the curved wall portion has a center of curvature thereof. The moving step then includes the positioning of the source and of the array at each step along a respective arc curved about the center of the vessel. Preferably, the detecting step detects over a limited angle greater than ±30°.

If desired, the array and source can be reoriented relative to a new wall portion after the further datasets for the tomogram of the initial wall portion are obtained. Then by repeating the detecting and moving steps, an inspection of the new wall portion can be easily obtained. Further, the source and array can be indexed in a direction perpendicular to a plane including the limited angle in a plurality of steps. Then, by repeating the detecting and moving steps at each index step, a tomogram can be obtained of the wall portion at each step and hence a three dimensional image can be created of the wall portion.

It is an advantage of the present invention that a non-destructive inspection of a portion of a large and heavy curved wall of a pressure vessel or the like for defects is achieved.

It is also an advantage of the present invention that a series of tomograms can be taken to provide for a full inspection of various areas of interest in the wall of a pressure vessel or the like.

It is a further advantage of the present invention that areas which were hitherto incapable of inspection can now be inspected.

It is a still further advantage of the present invention that defects of small size can be detected and hence repaired, contributing to reduced initial defect size in the vessel and enhanced reliability of the vessel.

It is still another further advantage that an improved inspection is achieved over the prior art advanced crack-tip-diffraction ultrasonic testing (UT) technique which is currently being used on vessels of this type. A defect size as small as 0.010"–0.025" can be detected by the present invention in contrast to a typical 0.150" defect inspection limit of the current advanced UT technique.

Due to the large grain sizes of some Inconel weld deposited cladding, the advanced UT beams are deflected causing ambiguous signals, while the focused longitudinal ultrasonic wave with its longer wave length is less sensitive to detecting defects. It is yet another advantage that the present invention has no such limitations.

Other features and advantages of the present invention are stated in or apparent from a detailed description of a presently preferred embodiment of the invention found hereinbelow.

DETAILED DESCRIPTION OF THE PREFERRED EMBODIMENTS

Figure 1:
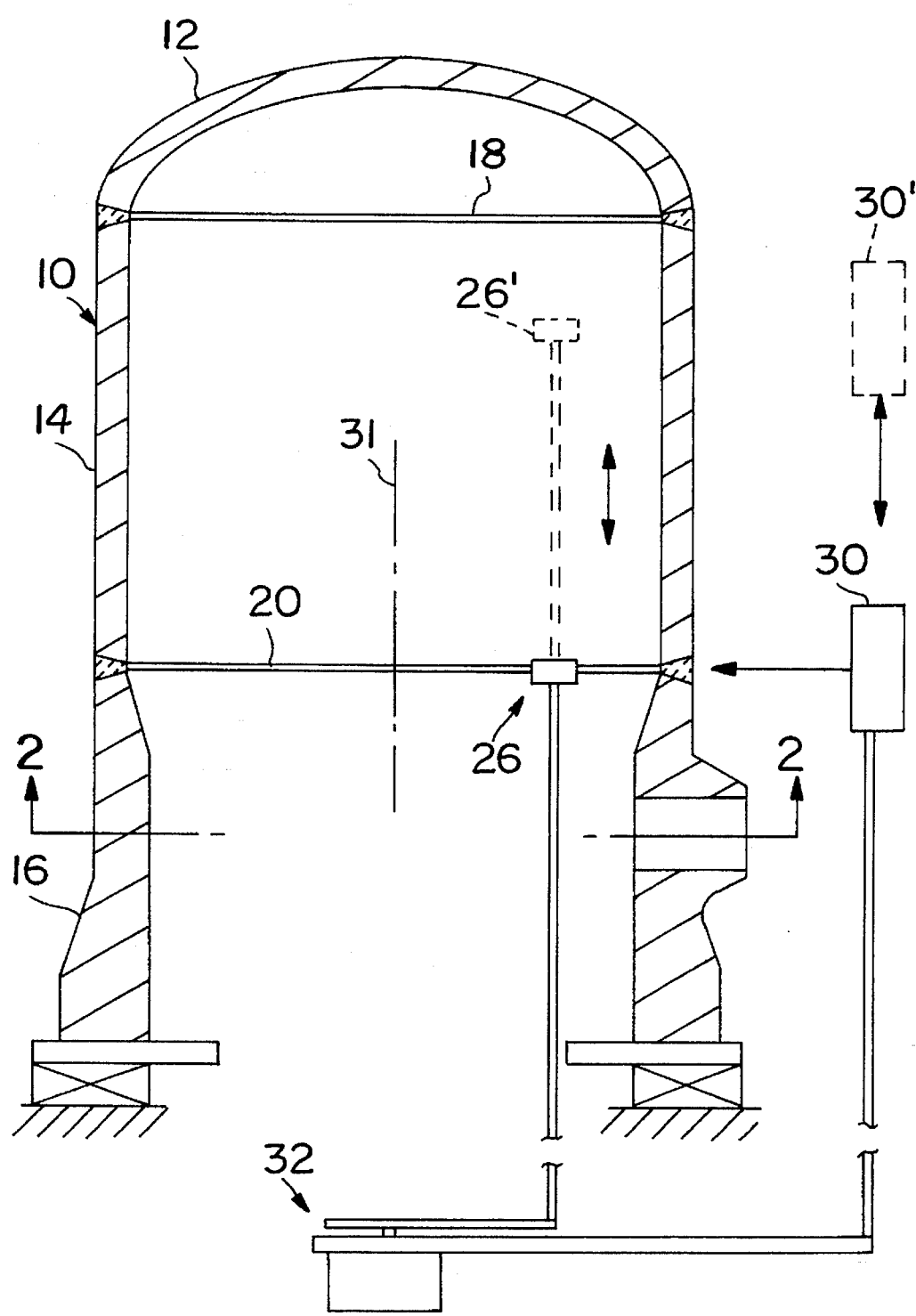
FIG. 1 is a schematic cross-sectional elevation view vessel being inspected in accordance with the present invention.
Figure 2:
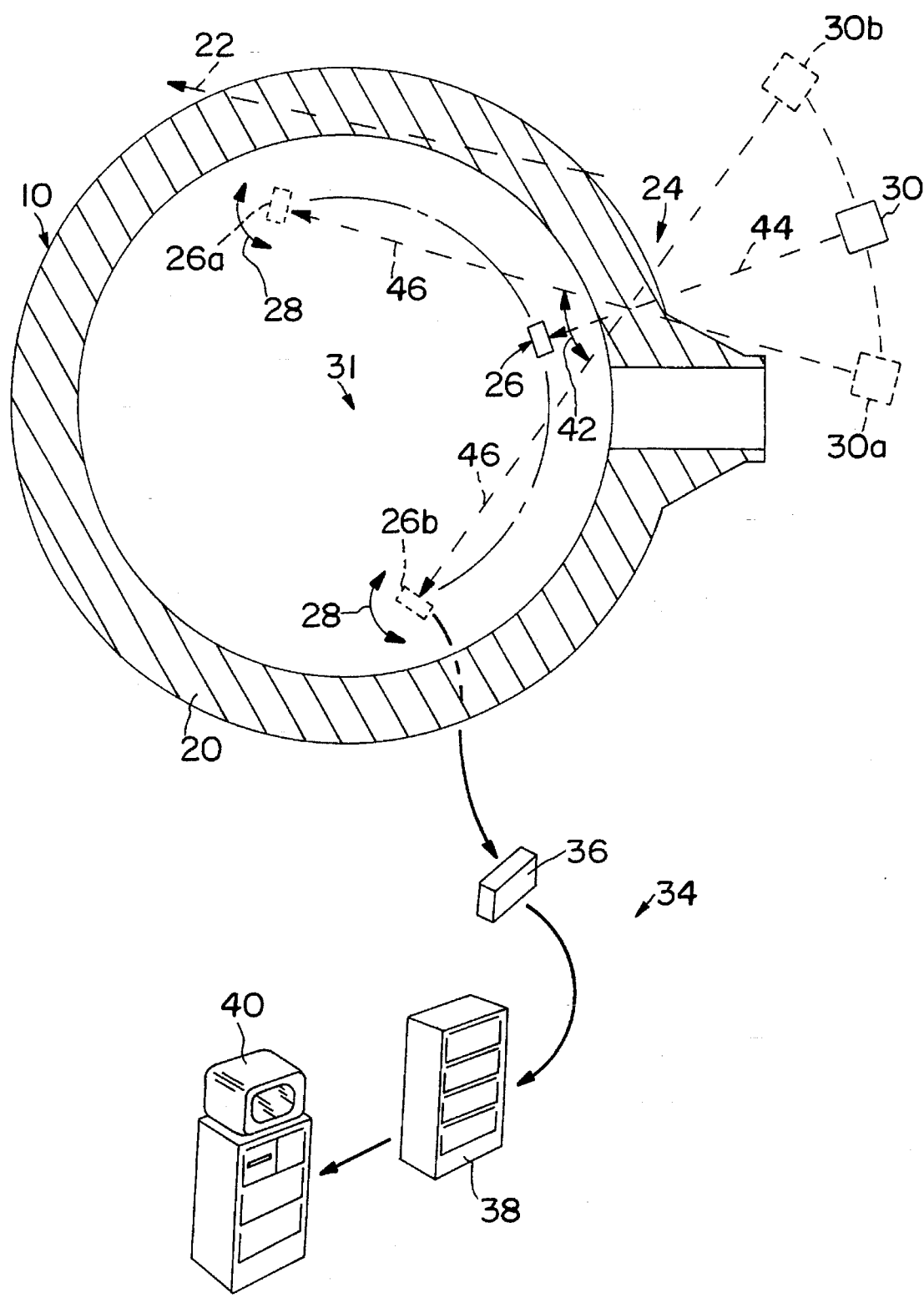
FIG. 2 is a cross-sectional plan view of the vessel depicted in FIG. 1 taken along the line 2—2 in FIG. 1.

With reference now to the drawings in which like numerals represent like elements throughout the two views, a steel pressure vessel 10 such as used to house a nuclear reactor is depicted in FIGS. 1–2. Vessel 10 is a weldment of a head 12, a middle 14, and a base 16 (as oriented in FIG. 1). Vessel 10 is suitably supported at appropriate locations at the base, with the center unobstructed from below. As shown, head 12, middle 14, and base 16 have been welded together by welds 18 and 20. Welds 18 and 20 are sources of defects (voids, cracks, etc.), and thus it is desirable to inspect welds 18 and 20 for any such defects. However, the size of vessel 10 (for example on the order of 170" high, with a wall thickness of base 16 equal to 10.75" and with a wall thickness of middle 14 equal to 5.6") makes the use of a conventional CT impossible. As shown by path 22, the chord thickness through one side of vessel 10 can be extremely long, with this massive metal path serving to stop all photons which might be directed along path 22 and thus rendering any CT scan impossible.

The present invention is a method for obtaining a "limited angle" CT scan of a wall portion 24 of vessel 10. To accomplish this, an array or series 26 of small detectors is disposed or placed inside of vessel 10 at the height of weld 20. Disposed or placed outside of vessel 10 horizontally opposite to array 26 is a collimated source 30 of suitable photons (x-rays). In the preferred embodiment, array 26 and source 30 are mounted by a suitable moving means 32 (such as turntables or the like) to move in a coordinated manner about a central vertical (longitudinal) axis 31 of vessel 10 in predetermined increments or steps. As shown schematically in FIG. 2, array 26 is connected to a suitable tomographic analyzing apparatus 34 comprising a suitable interface 36, a computer system 38, and an associated display and memory system 40. Suitable analyzing apparatus 34 are well known in the art and available from various commercial companies such as ARACOR of Sunnyvale, Calif., BIO-IMAGING RESEARCH, INC. of Lincolnshire, Ill., SCIENTIFIC MEASUREMENT SYSTEMS of Austin, Tex., and IRT CORP. of San Diego, Calif.

When operated, source 30 and array 26 (as best seen in FIG. 2) are moved as a coordinated unit (in opposite directions) about central axis 31 in small increments or steps. The extremes of the steps are shown (in phantom) by the relative positions of source 30a and array 26a at one rotational extreme and the positions of source 30b and array 26b at the other rotational extreme. At each step of the coordinated rotation, source 30 is activated to emit photons which are detected by the detectors of array 26. For proper alignment, moving means 32 also includes a means for moving array 26 to directly face source 30 as shown schematically by arrows 28.

It will be appreciated that the detectors of array 26 only detect photons from source 30 over the extent of limited angle 42, drawn from a point in the center of wall portion 24 and on either horizontal side from a line 44 perpendicular to wall portion 24 and passing through source 30 and axis 31. Angle 42 depends on the size of the vessel being inspected and is only limited by the curvature of the wall of the vessel. In the preferred embodiment, angle 42 is from −45° to +45° inclusive from either side of line 44. This reduces the chord lengths of wall portion 24 which must be passed through by the photons to a reasonable value. This is an order of magnitude less than that which would be encountered by a conventional CT scan at the extreme ends of a scan.

By incrementally moving source 30 and array 28 about axis 31, at each incremental step the detectors of array 26 each detect the photons received thereby and produce a single dataset for each step. Then, as source 30 and array 26 are moved to a new position (step), a series of predetermined datasets are obtained for wall portion 24, up to the chosen limit imposed by limited angle 42 (as shown by the dotted lines 48). Once all of the steps between the limits of angle 42 are completed, analyzer apparatus 34 is used in the known manner to create a computer tomogram of wall portion 24 from the available datasets. It will be appreciated that the edges of wall portion 24 will not have enough datasets to produce a usable image at that location, but with additional datasets from subsequent wall portions and associated movements of source 30, this area can also be suitably and subsequently imaged.

Feasibility of this limited angle tomography inspection was demonstrated in a series of experiments using 2.5"–4" mating steel plates containing machined flaws of varying sizes and inspected by x-rays using tomographic analyzer Model 101B made by Scientific Measurements Systems, Inc. of Austin, Tex., which uses a Co-60 source and a 420 KeV x-ray source. These tests were performed using worst case scenarios for these plates. It will also be appreciated that the source energy is well suited for such tests.

Using this worst-case test, the datasets are available over only ±45° of wall portion 24, less than half those datasets normally used to produce a conventional ±90° computer tomogram. However, even in this worst-case test, it was shown that the information loss without the usual coverage of datasets over ±90° was found to be negligible, and the sensitivities achieved in measuring positions and dimensions of resolved features was about 0.01" perpendicular to the viewing direction and about 0.025" parallel to the viewing direction. This is more than satisfactory in determining the presence of defects, which then must be corrected. A hairline crack in a fatigue test specimen was also shown to be easily detected using this limited angle method, but it was not detected by the current advanced UT technique.

By suitably moving source 30 and array 26 around the entirety of vessel 10 to image succeeding wall portions, a series of overlapping tomograms of wall portions are produced so that the entire weld is inspected. In addition, moving means 32 is also capable of moving source 30 and array 26 vertically in vessel 10 as shown schematically by array 26' and source 30'. This obviously allows weld 18 to be scanned for a single tomogram of a wall portion or for a series of tomograms of the weld. Further, by vertical movements in small increments, a three dimensional image of weld 20 is provided by forming a series of vertically closely spaced tomograms.

While the present invention has been depicted with an array of detectors and a fan shaped source, other equivalent mechanisms to produce a tomogram well known in the art are also possible. Thus, a source with a collimated beam movable to project the beam in a fan shaped plane and/or a single detector movable to detect the collimated beam or portions of a fan shaped beam are possible. An array larger than the limited angle 42 (such as circular) could also be used, with the data from detectors beyond the limited angle simply ignored so that it would not be necessary to move the array each time the source is moved (and not to move the array at all if circular). In addition, it is possible to move the vessel instead of the source or array— though this is deemed unworkable in view of the large weight of vessel 10.

It is also believed that the present invention will be useful in the inspection of vessels for cladding defects or the like where cracks must be detected.

While the present invention has been described with respect to an exemplary embodiment thereof, it will be understood by those of ordinary skill in the art that variations and modifications can be effected within the scope and spirit of the invention.

I claim:

1. A method of non-destructively inspecting a curved wall portion for a defect, said wall portion having a center of curvature thereof, by producing a tomogram of the wall portion comprising the steps of:

placing a collimated source of radiation adjacent one side of the wall portion;

placing an array of detectors for the radiation on the other side of the wall portion adjacent the source;

detecting the radiation from the source passing through the wall portion with the detectors over a limited angle from a normal to the wall portion from the source to obtain a dataset;

moving of the source and array relative to the wall portion in steps between projected vertices of the limited angle, wherein said moving step comprises positioning of the source and the array of detectors at each step along respective arcs curved about the center of curvature, and obtaining at each step a further dataset;

processing of the plurality of datasets obtained over the limited angle to produce a tomogram of the wall portion and hence to determine the presence of a defect in the wall portion.

2. A method of inspecting as claimed in claim 1 wherein said detecting step detects over a limited angle from about −45° to +45° inclusive.

3. A method of inspecting as claimed in claim 1 and further including the steps of reorienting the detector array and source relative to a new wall portion after the further datasets for the tomogram are obtained and repeating the detecting and moving steps to obtain an inspection of the new wall portion.

4. A method of inspecting as claimed in claim 1 and further including the step of indexing the source and array in a direction perpendicular to a plane including the limited angle in a plurality of steps and repeating the detecting and moving steps at each index step to obtain a tomogram of the wall portion at each step and hence to create a three dimensional image of the wall portion.

5. A method of inspecting as claimed in claim 1 wherein the curved wall is part of a vessel; and wherein said placing steps place the source outside of the vessel and the detector array inside of the vessel.

6. A method of inspecting as claimed in claim 5 wherein said detecting step detects over a limited angle from about −45° to +45° inclusive.

7. A method of inspecting as claimed in claim 5 and further including the steps of reorienting the detector array and source relative to a new wall portion of the vessel after the further datasets for the tomogram are obtained and repeating the detecting and moving steps to obtain an inspection of the new wall portion.

8. A method of inspecting as claimed in claim 5 and further including the step of indexing the source and the detector array in a direction perpendicular to a plane including the limited angle in a plurality of steps and repeating the detecting and moving steps at each index step to obtain a tomogram of the wall portion at each step and hence to create a three dimensional image of the wall portion.

* * * * *